(12) United States Patent
Oobayashi et al.

(10) Patent No.: US 10,019,690 B2
(45) Date of Patent: Jul. 10, 2018

(54) INTELLECTUAL-PRODUCTIVITY ANALYSIS APPARATUS AND PROGRAM

(71) Applicant: Panasonic Corporation, Osaka (JP)

(72) Inventors: Fumiaki Oobayashi, Osaka (JP); Mikio Iwakawa, Osaka (JP); Hiroshi Shimoda, Kyoto (JP); Hirotake Ishii, Kyoto (JP); Kazune Miyagi, Kyoto (JP); Kotaro Oishi, Tokyo (JP); Shutaro Kunimasa, Nara (JP); Kosuke Uchiyama, Kyoto (JP); Kyoichi Seo, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 702 days.

(21) Appl. No.: 14/418,265

(22) PCT Filed: Jul. 8, 2013

(86) PCT No.: PCT/JP2013/004217
§ 371 (c)(1),
(2) Date: Jan. 29, 2015

(87) PCT Pub. No.: WO2014/034005
PCT Pub. Date: Mar. 6, 2014

(65) Prior Publication Data
US 2015/0154523 A1    Jun. 4, 2015

(30) Foreign Application Priority Data

Aug. 31, 2012  (JP) ................................ 2012-191746
Feb. 21, 2013  (JP) ................................ 2013-032328
May 21, 2013  (JP) ................................ 2013-107407

(51) Int. Cl.
*G06Q 10/06*    (2012.01)
*A61B 5/16*     (2006.01)
*G09B 7/02*     (2006.01)

(52) U.S. Cl.
CPC ........... *G06Q 10/0639* (2013.01); *A61B 5/16* (2013.01); *G09B 7/02* (2013.01)

(58) Field of Classification Search
CPC ......... G06Q 10/00; G06Q 40/06; G06F 17/60
(Continued)

(56) References Cited

U.S. PATENT DOCUMENTS 7,295,124 B2 * 11/2007 Guillen .................... A61B 5/16
340/539.12
2003/0200043 A1    10/2003 Wen et al.
(Continued)

FOREIGN PATENT DOCUMENTS

JP     09-135826 A    5/1997
JP    2001-120522 A   5/2001
(Continued)

OTHER PUBLICATIONS

International Search Report for corresponding International Application No. PCT/JP2013/004217 dated Aug. 13, 2013.
(Continued)

*Primary Examiner* — Romain Jeanty
(74) *Attorney, Agent, or Firm* — Renner, Otto, Boisselle & Sklar, LLP

(57) ABSTRACT

An intellectual-productivity analysis apparatus includes a presentation device, an input device, and an evaluation device. The presentation device presents a plurality of questions to a test subject. The input device allows the test subject input an answer to each question. The evaluation device includes a work memory part and an evaluating arithmetic part. The work memory part stores the answering
(Continued)

time from a time when a question is presented on the presentation device to a time when the answer is inputted into the input device for each of the plurality of questions. The evaluating arithmetic part calculates an evaluation value on the intellectual productivity of the test subject during a measurement period of measuring the answering time of each of the plurality of questions by extracting a feature amount from the set of the answering time stored in the work memory part.

17 Claims, 7 Drawing Sheets

(58) Field of Classification Search
USPC .............................................. 705/7.38, 7.11
See application file for complete search history.

(56) References Cited

U.S. PATENT DOCUMENTS

| | | | |
|---|---|---|---|
| 2004/0186765 A1* | 9/2004 | Kataoka | G06Q 10/06 705/7.29 |
| 2005/0053904 A1 | 3/2005 | Shephard et al. | |
| 2005/0125275 A1* | 6/2005 | Wright | G06Q 10/063114 705/7.15 |
| 2005/0191609 A1 | 9/2005 | Fadel et al. | |
| 2006/0074340 A1 | 4/2006 | Murata | |
| 2011/0151425 A1* | 6/2011 | Smith | G09B 7/00 434/350 |

FOREIGN PATENT DOCUMENTS

| | | |
|---|---|---|
| JP | 2002-140429 A | 5/2002 |
| JP | 2005-070169 A | 3/2005 |
| JP | 2006-087743 A | 4/2006 |

OTHER PUBLICATIONS

Form PCT/ISA/237 for corresponding International Application No. PCT/JP2013/004217 dated Aug. 13, 2013.
Extended European Search Report dated Jul. 13, 2015 for corresponding European Application No. 13832354.8.
Miyagi et al., "Development of an Evaluation Method for Office Work Productivity", Jul. 19, 2009, Engineering Psychology and Cognitive Ergonomics, Springer Berlin Heidelberg, Berlin, Heidelberg, pp. 101-110.
"Summons to attend oral proceedings pursuant to Rule 115(1) EPC dated Nov. 14, 2017 issued for the corresponding European Patent Application No. 13832354.8".

* cited by examiner

INTELLECTUAL-PRODUCTIVITY ANALYSIS APPARATUS AND PROGRAM

TECHNICAL FIELD

The present invention relates to an intellectual-productivity analysis apparatus that is configured to measure an intellectual productivity of a worker performing a mental task, and a program for realizing, to a computer, a function of an main part of the intellectual-productivity analysis apparatus.

BACKGROUND ART

Conventionally, there is known, as a technology that measures a recognition capability of a test subject, a technology that shows, to the test subject, an image generated by degrading an image including a meaningful object, and calculates a capability score with a time period (sensation time period) until the test subject perceives the object (for example, see JP 2006-87743 A, hereinafter, referred to as a "first document"). The first document discloses a technology that calculates beforehand difficulty information at the time of perceiving the image by showing the image to two or more persons, and calculates the capability score of the test subject by using the difficulty information of the image and the sensation time of showing the image to a specific test subject.

In order to measure a concentration of a test subject, there is proposed a technology that makes a test subject trace a standard figure and calculate a concentration ratio with a shift amount between the standard figure and a traced figure (for example, see JP 09-135826 A, hereinafter, referred to as a "second document"). The concentration ratio is calculated as a value obtained by multiplying, by the coefficient, a value calculated from the shift amount between the standard figure and the traced figure. Then, when the trace work is finished, a change, an average value, a standard deviation, a coefficient of variation, a maximum value, a minimum value, and the like of the concentration ratio, which are calculated at constant intervals during the trace work, are calculated. The second document discloses changing difficulty by changing a speed of the trace work when the trace of a standard figure is performed, and presuming a physiology state or a personality characteristic of the test subject by performing the trace work of the standard figure.

The capability score disclosed in the first document only expresses the capability to perceive the meaning of each image. Therefore, it is hard to evaluate, with the capability score, an intellectual productivity when the mental task load is given to the test subject.

On the other hand, if the technology disclosed in the second document is adopted, it is possible to calculate change of the concentration ratio of the test subject while a problem called the trace work is performed. However, since being not the mental task load, the trace work is not suitable for the evaluation of the intellectual productivity. The trace work depends on a hand's athletic ability of the test subject. In this point, the trace work is not suitable for the purpose of evaluating the intellectual productivity.

SUMMARY OF INVENTION

An object of the present invention is to provide an intellectual-productivity analysis apparatus, which can calculate an objective evaluation value concerning an intellectual productivity. Further the object of the present invention is to provide a program for realizing, to a computer, a function of a main part of the intellectual-productivity analysis apparatus.

An intellectual-productivity analysis apparatus according to the present invention includes a presentation device, an input device, and an evaluation device. The presentation device is configured to present a plurality of questions to a test subject. The input device is configured to allow the test subject input an answer to each of the plurality of questions. The evaluation device is configured to measure an answering time from a time when a question is presented on the presentation device for each of the plurality of questions to a time when the answer is inputted into the input device, the evaluation device being configured to calculate an evaluation value on an intellectual productivity of the test subject using a set of the answering time. The evaluation device includes a work memory part and an evaluating arithmetic part. The work memory part is configured to store the answering time for each of the plurality of questions. The evaluating arithmetic part is configured to calculate an evaluation value on the intellectual productivity of the test subject during a measurement period of measuring the answering time of each of the plurality of questions by extracting a feature amount from the set of the answering time stored in the work memory part.

In the intellectual-productivity analysis apparatus, preferably, the evaluating arithmetic part includes a histogram generating part, an applying part, and a calculation part. The histogram generating part is configured to classify the answering time into a plurality of sections. The histogram generating part is configured to regard, as a time occupancy degree, a ratio of a total of the answering time in a section to a total of the answering time for each of the plurality of sections. The histogram generating part is configured to generate a time occupancy degree histogram expressing distribution of the time occupancy degree. The applying part is configured to regard the time occupancy degree histogram as a superimposition of a first time occupancy degree histogram in a state where a working state and a short-term rest state are mixed, and a second time occupancy degree histogram in a state where the working state, the short-term rest state, and a long-term rest state are mixed. The applying part is configured to apply a probability density function of a log normal distribution to a candidate of the first time occupancy degree histogram among mountain-shaped regions with a peak of the time occupancy degree. The calculation part is configured to extract an expected value calculated from the probability density function as the feature amount, and calculate, as a concentration time, a product of the feature amount and a total number of the answers. The calculation part is configured to calculate the concentration time to the measurement period as the evaluation value.

In the intellectual-productivity analysis apparatus, preferably, the applying part is configured to apply, to the probability density function, a region where the time occupancy degree is not only smaller than the peak but also shorter than the answering time corresponding to the peak among the mountain-shaped regions.

In the intellectual-productivity analysis apparatus, preferably, the applying part is configured to, after applying the probability density function to the mountain-shaped regions, calculate a histogram except a portion equivalent to the probability density function from the time occupancy degree histogram. The applying part is configured to calculate a function applied to the histogram.

In the intellectual-productivity analysis apparatus, preferably, the calculation part is configured to calculate a value obtained by subtracting the concentration time from the measurement period as a non-concentration time in the measurement period.

In the intellectual-productivity analysis apparatus, preferably, the evaluating arithmetic part is configured to calculate a ratio of the concentration time to the measurement period as an evaluation value of a concentration ratio. The evaluating arithmetic part is configured to calculate a change of the concentration ratio of the test subject in two or more measurement periods.

Preferably, the intellectual-productivity analysis apparatus further includes a display device. The display device is configured to display, on a screen, a graph showing the answering time and the evaluation value calculated by the evaluating arithmetic part.

In the intellectual-productivity analysis apparatus, preferably, the presentation device and the input device are integrally provided with the evaluation device.

In the intellectual-productivity analysis apparatus, preferably, the feature amount is an amount so that a first state where the answering time is in a base period is dividable from a second state where the answering time exceeds the base period.

In the intellectual-productivity analysis apparatus, preferably, the feature amount is: a ratio of a total of frequency when the answering time is in the base period to a total of the plurality of questions; and a standard deviation calculated by applying to a log normal distribution, frequency distribution when the answering time is in the base period. The evaluating arithmetic part is configured to calculate the ratio as an evaluation value expressing a length of a time period of the first state. The evaluating arithmetic part is configured to calculate the standard deviation as an evaluation value expressing a concentration ratio of the time period of the first state.

In the intellectual-productivity analysis apparatus, preferably, the evaluating arithmetic part is configured to calculate a first state where the answering time is in a base period and a second state where the answering time exceeds the base period according to a time course of the measurement period.

A program to function a computer as an evaluation device configured to make a presentation device present a plurality of questions and allow a test subject input an answer to each of the plurality of questions into an input device. The evaluation device is configured to measure an answering time from a time when a question is presented on the presentation device for each of the plurality of questions to a time when the answer is inputted into the input device. The evaluation device is configured to calculate an evaluation value on an intellectual productivity of the test subject using a set of the answering time. The program functions the computer as the evaluation device. The evaluation device includes a work memory part and an evaluating arithmetic part. The work memory part is configured to store the answering time. The evaluating arithmetic part is configured to calculate an evaluation value on the intellectual productivity of the test subject during a measurement period of measuring the answering time of each of the plurality of questions by extracting a feature amount from the set of the answering time stored in the work memory part.

According to the composition of the present invention, each of the plurality of questions, the answering time is collected which is to the time when the test subject inputs the answer to a question from the time when the question are presented to the test subject after, and the feature amount is extracted from the set of answering time. Therefore, it is possible to calculate the objective evaluation value on the intellectual productivity such as the degree of concentration or the duration in the concentration state when a mental task load is given to the test subject.

BRIEF DESCRIPTION OF DRAWINGS

Preferable embodiments according to the present invention will be described in more detail. Other features and advantages of the present invention will be better understood with reference to the following detailed description and the attached drawings.

DESCRIPTION OF EMBODIMENTS

First Embodiment

In an embodiment described below, a case is assumed, in which a test subject is a worker in an office, a student in an educational facility or a learning environment, or the like. The worker in the office mainly performs not a physical work obtaining a work result by a motion of a body but a mental task performed using knowledge, such as a document preparing, an information management, or a classifying work. Hereinafter, productivity in the mental task is referred to as an "intellectual productivity". The intellectual productivity receives an influence in a degree of the concentration at the time of the work (hereinafter, referred to as a "concentration strength") and a duration in a concentrated state (hereinafter, referred to as a "concentration time") in addition to individual knowledge and a capability of skill.

For example, in the case where a mental work-load as to the work is comparatively large, if an intellectual productivity is improved, it is required that mental resources used for the mental task is concentrated highly. Therefore, high concentration strength is required. On the other hand, in the case where the mental work-load is large although the mental task load is comparatively small, it is required that a state where the mental resources used for the mental work is concentrated is continued. Therefore, although the concentration strength decreases a little, a comparatively long concentration time is required.

Test subject is not limited to the worker in the office and may be a student in a school of a home, for example. In the present embodiment, terms such as "mental work-load", the "mental load", and "mental" are used according to definitions described in Japanese Industrial Standard "JIS Z8502-1994". The Japanese Industrial Standard "JIS Z8502-1994" is a standard based on international standard of International Organization for Standardization (ISO) "ISO 10075 (Ergonomic principle related to mental work-load-General terms and definitions)". The "mental stress" and the "mental" is defined in Japanese Industrial Standard "JIS Z8502-1994" as described below. The "mental stress" is a whole influence capable of be evaluated, which gives an effect on the human body from the outside and a mental effect.

The intellectual-productivity analysis apparatus described below is configured to calculate an evaluation value relevant to an intellectual productivity by presenting a plurality of questions to a test subject and making the test subject perform a series of work of inputting an answer for each question. This evaluation value is quantitatively calculated about at least one of concentration strength and a concentration time of the test subject.

Figure 1:
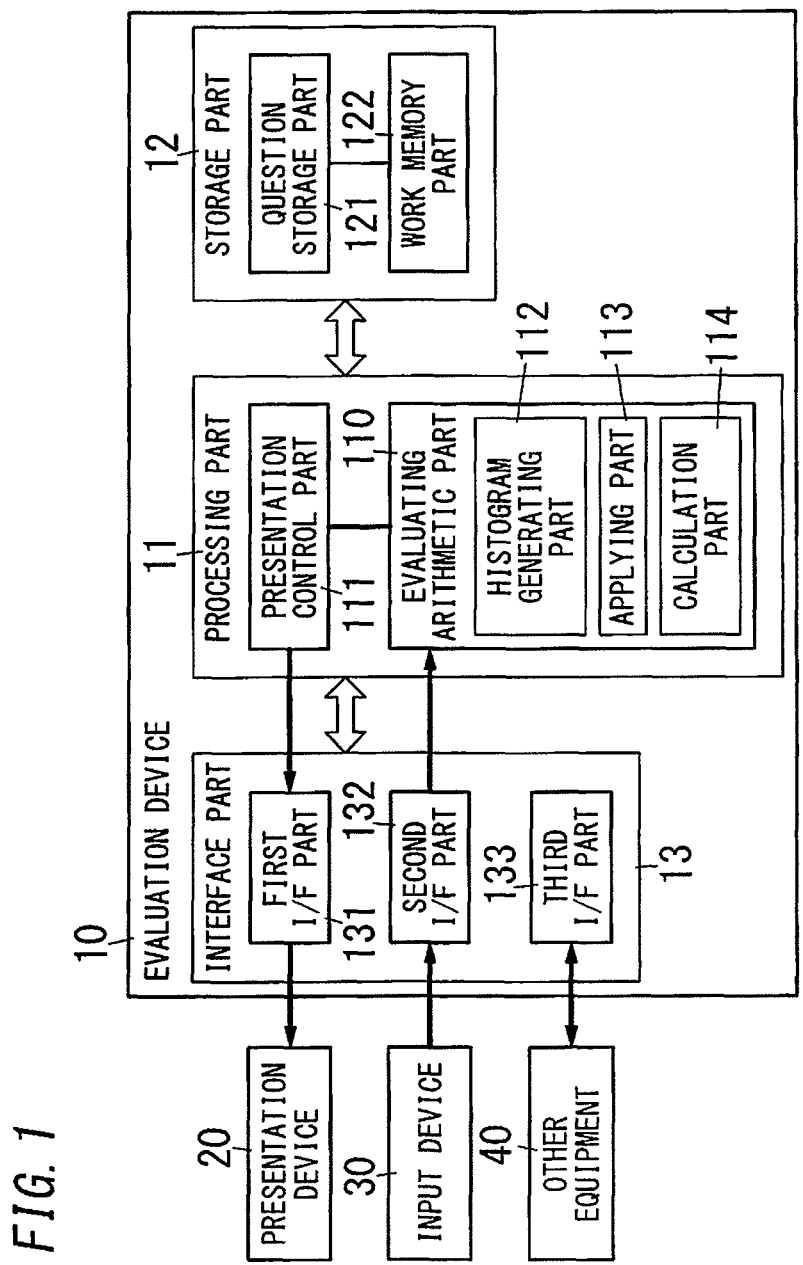
FIG. 1 is a block diagram illustrating an intellectual-productivity analysis apparatus according to a first embodiment.

As shown in FIG. 1, the intellectual-productivity analysis apparatus includes: a presentation device 20 that is configured to present questions; an input device 30 that is configured to allow the test subject input the answer to each question; and an evaluation device 10 that is configured to calculate the evaluation value relevant to the intellectual productivity of the test subject. The evaluation device 10 may be a dedicated device. Also, the evaluation device 10 may be realized by executing a program with a general-purpose computer. The computer may be a desktop type or a notebook type. Also, the computer may be a tablet terminal, a smart phone, or a game machine exchangeable a program.

When the computer of the notebook type, the tablet terminal, the smart phone, the game machine, or the like is used as the evaluation device 10, the evaluation device 10 may be integrally provided with the input device 30 at least. Further, the evaluation device 10 may be integrally provided with the presentation device 20 in addition to the input device 30. In short, any of the following three configuration is adopted: a configuration in which the evaluation device 10 is separately provided with the presentation device 20 and the input device 30; a configuration in which the evaluation device 10 is integrally provided with the input device 30; and a configuration in which the evaluation device 10 is integrally provided with the presentation device 20 and the input device 30.

When the input device 30 is separated from the evaluation device 10, a notebook computer, a tablet terminal, a smart phone, a game machine, or the like is used as the input device 30. When a plurality of options are presented by the input device 30, a time when the answer is inputted into the input device 30 is a time when any of the plurality of options is selected. On the other hand, when the test subject inputs the answer to the input device 30 with a stylus pen (touch pen) that is one of pointing devices, for example, the input device 30 displays, on an area different from an area for inputting the answer, an icon for informing the input device 30 and the evaluation device 10 of the completion of the input. Then, a time when the icon is clicked after the answer is inputted is a time when the answer is inputted to the input device 30.

When the presentation device 20 is separated from the evaluation device 10, an electronic paper or a paper may also be used as the presentation device 20. When the electronic paper is used as the presentation device 20 independently, or when the paper is used as the presentation device 20, the time at which the questions are presented cannot be measured precisely. Therefore, the presentation device 20 as which the electronic paper is used independently, or the presentation device 20 as which the paper is used is adopted when measuring simply.

When the pieces of paper is used as the presentation device 20, in order to identify a presented recognition object, identification information like QR Code (registered trademark) may be individually written for each of pieces of paper that presents the recognition object, for example. Then, this identification information may be read by a reader such as a camera. If this configuration is adopted, it is possible to measure a time when the recognition object is presented using a time when the reader reads the identification information.

When the electronic paper is used as the presentation device 20, a function of communicating with an external device different from the evaluation device 10 and the presentation device 20 may be added to the presentation device 20. In this configuration, if the external device outputs information for presenting the question to the presentation device 20, and the external device outputs, to the evaluation device 10, a time when the information is outputted, the time when the question is presented is measured precisely.

The presentation device 20 can adopt a configuration for presenting the plurality of questions at once. The presentation device 20 preferably adopts a configuration for presenting a question one by one. This is because it is convenient for measuring the answering time from a time when the question is presented by the presentation device 20 to a time when the answer is inputted into the input device 30 for each of the plurality of questions as described below. However, the answering time of the individual question may be the following time: a first answering time is a time period to a time when a first answer is obtained from a time when a list of the plurality of questions are presented; the other answering times are determined by using times between the answers.

A set of a plurality of questions (for example, 100 or more questions) used for one measurement is chosen so that the standard deviation about the mental load is in a prescribed range. In other words, in the state where people concentrate, the set of the plurality of questions is set so that the standard deviation of the answering time of each question is in a prescribed range. For example, it is possible to choose addition of single-digit numbers and addition of five-digit numbers as a question. However, the both do not form the same set since the mental stresses of the both differ substantially.

Each question presented by the presentation device 20 must be a question on which an answer is determined uniquely. However, the following question is hard to a question suitable for the measurement, in which has few kinds in question like an addition of single-digit numbers, and a difference in the characteristic of the answering time between the time of concentration and the time of non-concentration is not clear if a practice effect arises. The question presented by the presentation device 20 is desirably designed so that the difference in the characteristic of the answering time between the time of the concentration and the time of the non-concentration is clear even if the practice effect is saturated.

The set of the questions used for one measurement needs to include the question in which the standard deviation of the answering time over each question consists of in a stipulated range in the concentration state of a person. Each question needs to be designed so that the difference in the characteristic of the answering time with the time of concentration and non-concentrating may become clear.

In order to fulfill this condition, for example, the presentation device 20 presents a proper recognition object, and just to make into a question to discover from a choice the combination of two or more kinds of cognitive elements extracted as an attribute of a recognition object. In this case, an answer is chosen a suitable choice. The cognitive element means the attribute that the test subject without special knowledge can recognize about a recognition object. It is required that the recognition object should be provided with two or more kinds of such attributes.

For example, if the recognition object is made into a word, classification of the meaning of a word can be used as the cognitive element, and a character type (form of the character) expressing a word, the number of characters in the word, a sound on a specified position of the word, and a color, a size, and a style of the character, for example, can be also used as the cognitive element. On the other hand, a figure, a sign, and a picture, for example, can be also used as the recognition object. About these recognition objects, a form, content, a color, and a size, for example, can be used as the cognitive element.

The question in the case where the presentation device 20 presents the recognition object includes: a first work of extracting the cognitive element that is included in the question; and a second work of choosing the option suitable for the cognitive element extracted from the question. Since the recognition object includes two or more kinds of cognitive elements (m kind, m>=2), the first work is a work of extracting two or more kinds of predetermined cognitive elements (n kind, 2<=n<=m) demanded as the answer among the two or more kinds of cognitive elements. Each of the two or more kinds of prescribed cognitive elements has two or more selections. The second work is a work of choosing the option suitable for the cognitive element extracted in the first work among the options. The number of the options is the number of the combinations of the two or more selections in each of the two or more kinds of prescribed cognitive elements. That is, when the recognition object is given, the question (problem) is to perform the first work and the second work.

In this case, the two or more kinds of selections are set for each cognitive element, and the options of the answer is set with the combination of selections. Therefore, the test subject inputs, into the input device 30, the option selected in the second work as the answer. Incidentally, in order to evaluate the intellectual productivity, it is important that the measurement accuracy is also suitable. On that account, it is required for the cognitive load of the work question is suitable. In order to give the test subject the suitable cognitive load, about three or four kinds of the cognitive elements are desirable because of the following reason. The cognitive load is too low in two kinds of the cognitive elements. On the other hand, the cognitive load is too high in too many cognitive elements. Therefore, hindrance factor, such as volition deterioration to the work question, occurs easily.

If three selections are set for each cognitive element, and the number of cognitive elements is two, nine options (=3×3) is obtained in the combination of two kinds of the cognitive elements (n=2), twenty seven options (=3×3×3) is obtained in the combination of three kinds of the cognitive elements. Therefore, the recognition object is desirably presented so that three or more kinds of cognitive elements are capable of being extracted. If the recognition object is the word (in the Japanese, the word written in Kana), the selection of the recognition object is easy, and the kind of the recognition object is also abundant. Therefore, it is possible to measure the concentration ratio so that the bias as to the recognition object does not occur by choosing the recognition object from a large range.

For example, it is assumed that the recognition object presented to the test subject is the word "BOOK", and the cognitive elements are the following three kinds of elements: a font; a first vowel; and a meaning. The presentation device 20 presents the word "BOOK" with a font of sans-serif. The selections of the font are serif, sans-serif, and script. The selections of the first vowels are "i", "u", and "e". The selections of the meaning are an animal/plant, a name of a place/person, and artificiality. In this example, there are three kinds of cognitive elements and three selections for each cognitive element. Therefore, twenty seven options are provided in total. In this example, the option of a correct answer is a combination of sans-serif, "u", and artificiality. Therefore, the test subject should input this option as the answer into the input device 30. In the case where the input device 30 includes a screen, twenty seven options should be arranged on the screen, and the test subject should choose the correct answer.

When the recognition object presented to the test subject is Japanese word, a character type may be used instead of the font as the cognitive element. The selections of the character type may be hiragana, katakana, and Chinese character. The number of characters may be used instead of the character type as the cognitive element. The number of characters may be three characters, four characters, and five characters.

The task described above is a word classification task of answering to the question that classifies the word about the two or more kinds of cognitive elements. When an apparatus including a display and an operation unit is used, an easy numerical calculation may be used as the question. For example, if the operation unit is operated after the addition numbers displayed on the display is stored, an augend is displayed on the display, and the mental-arithmetic addition task is considered, which sets, as a work per question, the work of calculating the sum of the addition number and the augend in mental arithmetic and inputting from the operation unit. In the case of an addition of about two-digit numbers, the answering time per question is about 2 to 5 seconds, and the question is a comparatively good work.

Figure 2A:
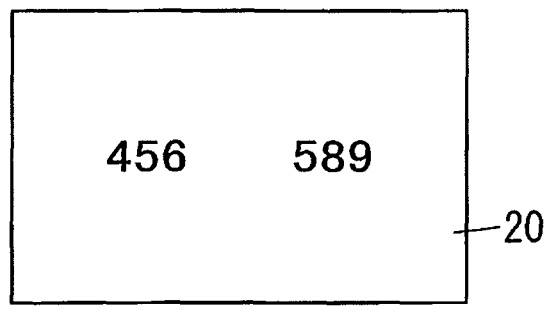
FIG. 2A is a drawing illustrating an example of a recognition object according to the first embodiment.
Figure 2B:
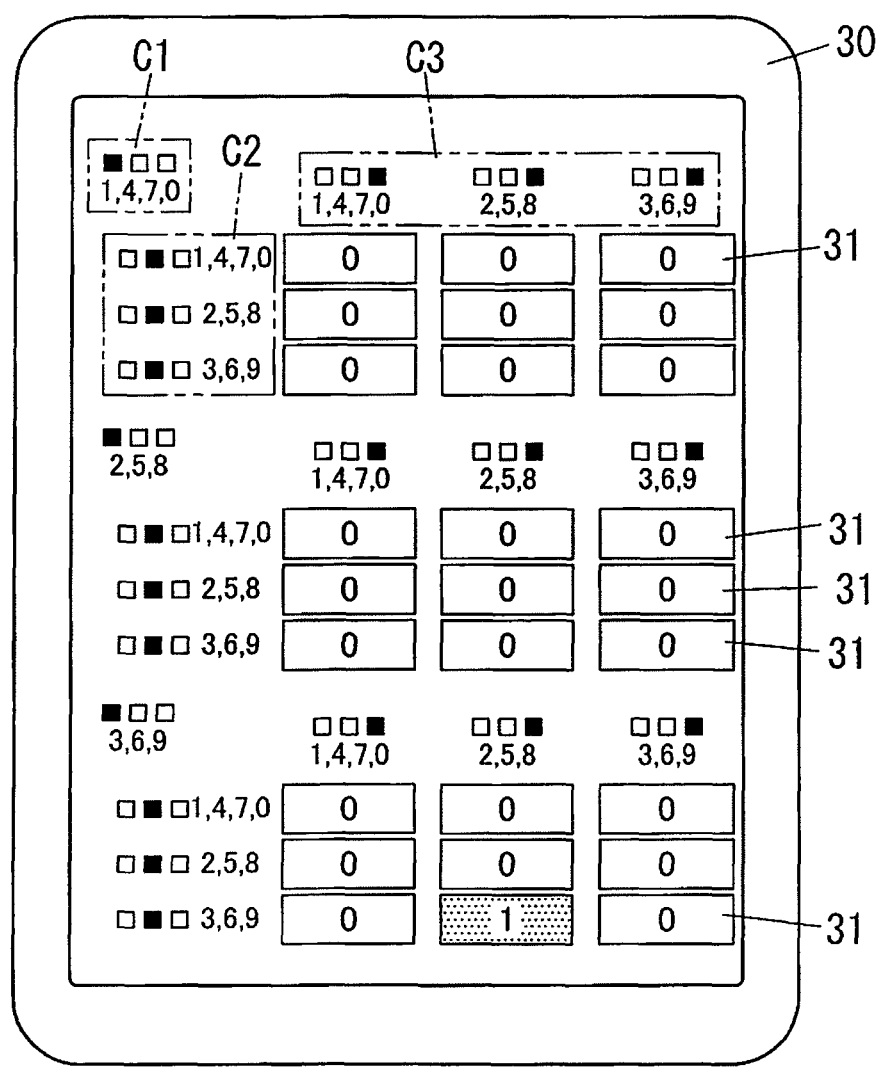
FIG. 2B is a drawing illustrating a display example of an input device according to the first embodiment.

Further, in the case where the cognitive element is number, FIG. 2A shows another example of the cognitive element presented to the test subject, and FIG. 2B shows a display example options used when the test subject inputs the answer. The cognitive elements are three kinds of number sets of (1, 4, 7, 0), (2, 5, 8), and (3, 6, 9) in the classify work to the number sets. Here, since the work of only classifying into the number sets to which each digit figure of the three-digit number belongs is too simple, a desire may decrease by the measurement of the concentration ratio is finished. Therefore, to maintain the desire to the work, a pair of three-digit numbers are presented, and simple four arithmetic operations using both of the numbers are combined.

Specifically, the following work is performed as for the pair of three-digit numbers: the addition of figures of left ends (third digit), the addition of figures of center (second digit), and the addition of figures of right ends (first digit); and adopting figure of ones place in number obtained by each addition. In an example shown in FIG. 2A, the numbers are (456) and (589). Therefore, the addition of the figures of the left ends is 4+5=9, and then, "9" in the ones place is adopted. The addition of the figures of the center is 5+8=13, and then, "3" in the ones place is adopted. The addition of the figures of the right ends is 6+9=15, and then, "5" is adopted. That is, the figures used for performing the classifying work are "9", "3", and "5".

On the other hand, the figures of three digits are the cognitive elements, and the number of the cognitive elements is three. Therefore, the combinations of the cognitive elements cannot be indicated with two dimension matrix. For this reason, as shown in FIG. 2B, a group is formed, in which the figures of the left ends are the cognitive elements, and two dimension matrix is formed, in which the figures of the center and the figures of the right ends are the cognitive elements. That is, an example is shown in a region C1, the groups of three kinds of number sets, to which the figures of the left ends belong, are arranged up and down. Further, as for each group, nine options 31 are set, which are showed as the matrix composed of the combinations of the three kinds of number sets to which the numbers of the center shown in the region C2 as an example, and the three kinds of number sets to which the figures of the right ends shown in the region C3 as an example. Therefore, three groups is set, each which includes the nine options 31, and accordingly, twenty nine options in total is presented on one screen.

In the illustrated example, in order to show, as the cognitive element, the figure at which position of the recognition object, three squares are arranged right and left in each of regions C1, C2, and C3, and the positions of the cognitive elements are shown by the squares becoming black. For example, in the region C1, the square of the left end is black, and the figure of the left end is shown to be the cognitive element.

In the example described above, since the work of classifying the three-digit number (9, 3, 5), the lower group is selected, in which the figure of the left end is included in (3, 6, 9). Further, in the group, the position is selected, in which the figure of the center is included in (3, 6, 9) and the figure of the right end is included in (2, 5, 8). Accordingly, the shaded position is a right answer, at which "1" is written in the option.

The evaluation device 10 shown in FIG. 1 is used with the presentation device 20 and the input device 30, and configured to calculate the evaluation value as to the intellectual productivity by making the test subject perform the first work and second work as described above. The answering time from the time when the question is presented by the presentation device 20 to the time when the answer is inputted into the input device 30 is used for the evaluation of the intellectual productivity. When the test subject does not choose the correct answer to the question, the answering time over the question may be excluded from the evaluation of the intellectual productivity. Alternatively, the accuracy rate may be used as a weighting coefficient to the evaluation value as to the intellectual productivity. The evaluation value as to the intellectual productivity may decreases when the accuracy rate is low.

The evaluation device 10 includes a device including a processor that operates according to a program, and a device for an interface for connecting an external device, as main hardware elements. The device including the processor is selected from a microprocessor, a microcomputer, a DSP (Digital Signal Processor), an FPGA (Field-Programmable Gate Array), or the like. The device for the interface has a function of connecting the presentation device 20 and the input device 30 at least. Further, the device for the interface desirably has a function of communicating through a LAN (Local Area Network) or a WNA (Wide Area Network).

The program executed by the processor may be acquired not only through an electric telecommunication line like Internet, but also by reading a program stored in a readable medium by the computer.

The evaluation device 10 includes a processing part 11, a storage part 12, and an interface part 13, in the case of being divided into a functional order. The interface part (hereinafter, referred to as an "I/F part") 13 includes a first I/F part 131 and a second I/F part 132. The presentation device 20 is connected to the first I/F part 131. The input device 30 is connected to the second I/F part 132. The I/F part 13 of the present embodiment includes a third I/F part 133. The third I/F part 133 is connected to the wide area network or local area network represented by the Internet.

The storage part 12 includes a question storage part 121. The question storage part 121 is configured to store the two or more questions presented to the presentation device 20. The question storage part 121 is configured to store the correct answers that are respectively associated with the questions in addition to the questions. The processing part 11 includes a presentation control part 111. The presentation control part 111 is configured to select the questions used for one measurement among the two or more questions stored in the question storage part 121, and present the selected questions to the presentation device 20. The presentation control part 111 has also a function of making the presentation device 20 present the options according to each question.

The storage part 12 includes a work memory part 122. The work memory part 122 is configured to store, for each question, the time period from a time when the question is presented on the presentation device 20 to a time when the answer is inputted into the input device 30. The work memory part 122 is also configured to store the right or wrong of the answer for each question. That is, when the test subject inputs the answer into the input device 30 in a state where the question is presented on the presentation device 20, the work memory part 122 is configured to store the answering time and the right or wrong of the answer by the test subject. After the answers are obtained about a one-set of the questions, the processing part 11 is configured to calculate an answer rate of the set. The work memory part 122 is configured to store the answer rate. In the above-mentioned example, the work memory part 122 is configured to store both of the answering time and the right or wrong of the answer for each question. However, the work memory part 122 may be configured to store only the answering time.

The processing part 11 includes an evaluating arithmetic part 110. The evaluating arithmetic part 110 is configured to calculate the evaluation value about the intellectual productivity of the test subject. After the presentation device 20 presents one-set of the questions, and the work memory part 122 stores information that the test subject inputs into the input device 30, the evaluating arithmetic part 110 calculates the evaluation value about the intellectual productivity of the test subject using the information stored in the work memory part 122.

Hereinafter, the processing that the evaluating arithmetic part 110 performs will be described. The evaluating arithmetic part 110 is configured to convert the set of the answering time stored in the work memory part 122 in one measurement into the form that the characteristic of the answering time appears like a frequency distribution. It is possible to extract of the feature amount of the set of the answering time by converting the set of the answering time into another form. Therefore, it is possible to calculate the evaluation value concerning the intellectual productivity of the test subject from the feature amount. Hereinafter, the technology using the frequency distribution of the answering time will be described in order to calculate the evaluation value concerning the intellectual productivity.

Figure 3:
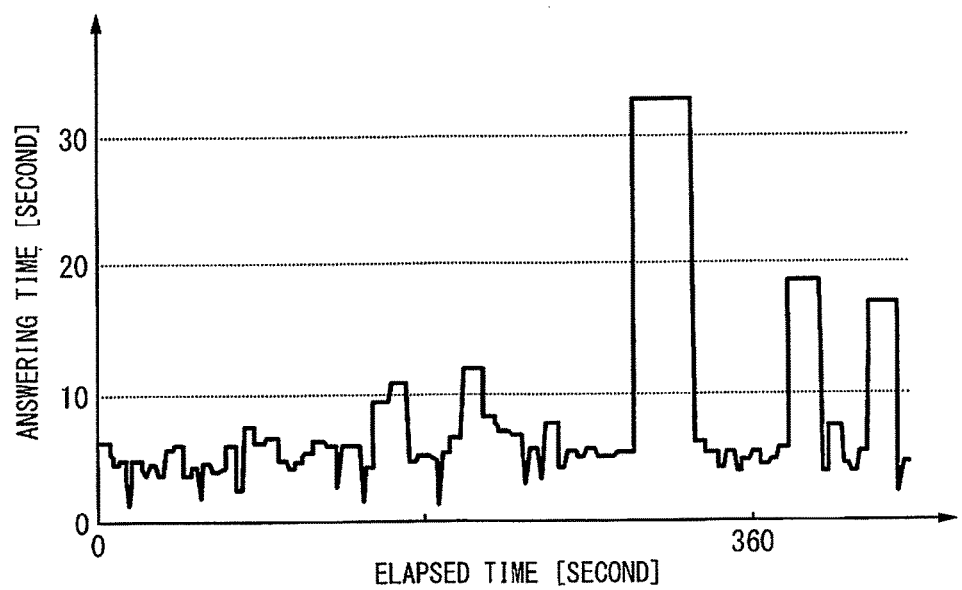
FIG. 3 is a drawing illustrating a relation between an elapsed time and an answering time in the intellectual-productivity analysis apparatus according to the first embodiment.

FIG. 3 shows an example in which the answering time stored in the work memory part 122 is expressed so as to be associated with the elapsed time from the start of one measurement. A horizontal axis in FIG. 3 expresses the elapsed time from the measurement start, and a vertical axis expresses the answering time to the input of the answer from the presentation of the question. In the illustrated example, when a period (left end part) in which the elapsed time from starting the measurement is short is compared with a period (right end part) in which the elapsed time is long, the answering times of the period (left end part) in which the elapsed time is short tend to be longer than those of the period (right end part) in which the elapsed time is long. This tendency is considered to mean that activation is declining by reduction in arousal of the test subject.

In the state where a person performs the intellectual work, the model described using three states of a "working state", a "short-term rest state" and a "long-term rest state" is considered. The "working state" is a state where the cognitive resources are assigned to the target (task target) and the processing of the work advances. The "short-term rest state" is a state where the processing of the work is stopped during the short-time unconsciously although the cognitive resources are assigned to the target. This state is physiologically generated in fixed probability. The "long-term rest state" is a state where the cognitive resources are not assigned to the target and the rest is taken during the long time.

Figure 4:
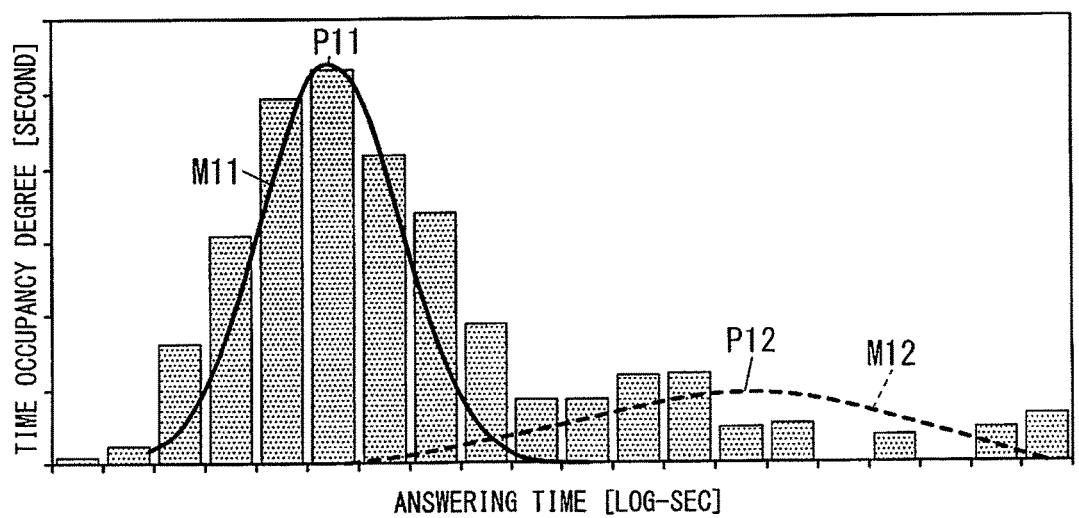
FIG. 4 is a drawing illustrating an example of a time occupancy degree histogram of a bimodal aspect used for the intellectual-productivity analysis apparatus according to the first embodiment.

The "working state" and the "short-term rest state" can be considered to be the concentration state since the cognitive resources are assigned to the target. The "long-term rest state" can be considered to be the non-concentration state since the cognitive resource is not assigned to the target. In order to evaluate the concentration state and the non-concentration state quantitatively, frequency distribution is calculated paying attention to the answering time stored in the work memory part 122. As a result, the time occupancy degree histogram as shown in FIG. 4 is obtained.

Figure 5:
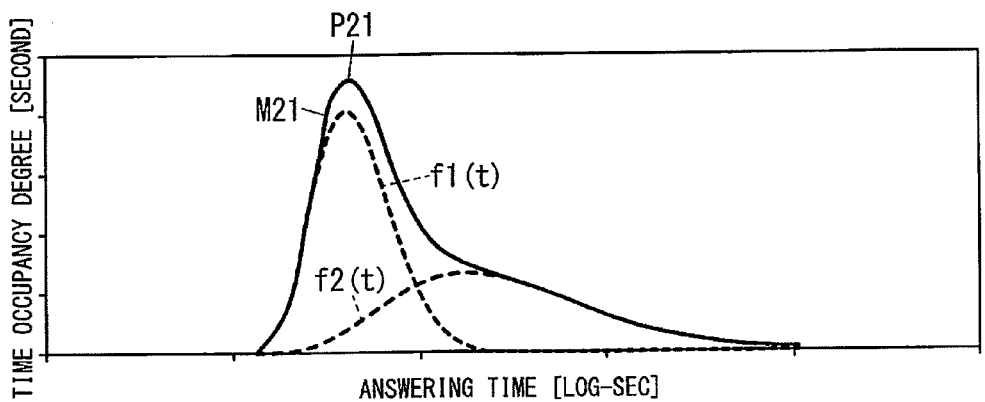
FIG. 5 is a drawing illustrating an example of a time occupancy degree histogram of a unimodal aspect used for the intellectual-productivity analysis apparatus according to the first embodiment.

The time occupancy degree histogram a histogram that denotes, as a time occupancy degree, a ratio of a total of a answering time for each section to the total of the answering time of all sections (measurement period) when the answering time are divided into two or more sections. A horizontal axis expresses the answering time with logarithmic scale, and a vertical axis expresses the time occupancy degree. In the case where the above-mentioned work is performed, the time occupancy degree histogram is a bimodal aspect provided with two mountain-shaped regions M11 and M12 at a glance as shown in FIG. 4. Alternatively, the time occupancy degree histogram is a unimodal aspect provided with one mountain-shaped region M21 as shown in FIG. 5. The time occupancy degree histogram of the bimodal aspect has two peaks P11 and P12, and the time occupancy degree histogram of the unimodal aspect has one peak P21.

Here, it is assumed that the time occupancy degree histogram is superimposed by a first time occupancy degree histogram in the state where the "working state" and the "short-term rest state" are mixed, and a second time occupancy degree histogram in the state where the "working state", the "short-term rest state", and the "long-term rest state" are mixed. That is, it is considered that the time occupancy degree histogram obtained based on the answering time is separable into the first time occupancy degree histogram and the second time occupancy degree histogram in spite of the time occupancy degree histogram of the bimodal aspect or the unimodal aspect, and the following processing is performed.

There is the knowledge that the form of the first time occupancy degree histogram in the state where the "working state" and the "short-term rest state" are mixed can be applied so as to be approximated to the probability density function of log normal distribution. On the other hand, there is a result that the form of the second time occupancy degree histogram in the state where the "working state", the "short-term rest state", and the "long-term rest state" are mixed has individual difference, and can be applied to log normal distribution arises. It is considered that this result occurs caused to the individual difference of the "long-term rest state".

Incidentally, it is considered that the test subject, which performs the work, makes an effort to maintain the concentration state. Therefore, the answering time, at which the time occupancy degree is the maximum, is presumed to reflect that the test subject is the state in which the "working state" and the "short-term rest state" are mixed. Therefore, it is considered that the difference between the following answering times is comparatively short: the answering time corresponding to the peaks P11 and P21 at which the time occupancy degrees are the maximum in the time occupancy degree histogram; and the answering time corresponding to the peak of the first time occupancy degree histogram. This difference is changed according to a distance (difference of the answering time) between the peak of the first time occupancy degree histogram and the peak of the second time occupancy degree histogram. There is the possibility that the difference increases as the distance is short. Here, the following is considered: the distance between the peak of the first time occupancy degree histogram and the peak of the second time occupancy degree histogram is comparatively long in the time occupancy degree histogram of the bimodal aspect; and the above-mentioned distance is comparatively short in the time occupancy degree histogram of the unimodal aspect.

On the other hand, the influence of the second time occupancy degree histogram is little in the region where the answering time is shorter than the peak P21 among the mountain-shaped region M21 including the peak P11, or the region where the answering time is shorter than the peak P21 among the mountain-shaped region M21 including the peak P21. Therefore, it may be considered that each of these regions is a part of the first time occupancy degree histogram.

Then, in the case of the time occupancy degree histogram of the bimodal aspect, in the mountain-shaped region M11, it is desirable to apply the range including the peak P11 and the region where the answering time is shorter than the peak P11 to the first time occupancy degree histogram. The range applied to the first time occupancy degree histogram may be included to the range in which the answering time exceeds about 10 to 15% to the answering time corresponding to the peak P11, although the range not more than the peak P11 is the minimum in the mountain-shaped region M11. About the time occupancy degree histogram of the unimodal aspect, if the mountain-shaped region M11 is read as the mountain-shaped region M21 and the peak P11 is read as the peak P21, it is possible like the time occupancy degree histogram of the bimodal aspect to apply to the first time occupancy degree histogram.

Here, the probability density function of the log normal distribution applied to the first time occupancy degree histogram is set to f1(t). The function applied to the second time occupancy degree histogram is set to f2(t). The function f(t) approximated to the time occupancy degree histogram is denoted by f(t)=f1(t)+f2(t). Here, the expected value of the function f1(t) is set to E, and the number of answers in the first time occupancy degree histogram is temporarily set to N1, and the number of answers includes in the second time occupancy degree histogram is temporarily set to N2.

In this case, an area S1 equivalent to the first time occupancy degree histogram is denoted by S1=E×N1. As described above, it is assumed that the second time occupancy degree histogram expresses the state where the "working state", the "short-term rest state", and the "long-term rest state" are mixed. Therefore, it is considered that an area S2 equivalent to the "short-term rest state" and the "working state" of the area of the second time occupancy degree histogram is denoted by S2=E×N2.

Since N1+N2 is a total of the number of answers, if N1+N2 is set to N1+N2=N, in the time occupancy degree histogram, the gross area S equivalent to the "working state" and the "short-term rest state" is expressed as S=S1+S2=E×N. The calculated total area S is equivalent to the total time (concentration time) of the concentration state. That is, the ratio of the total area S of the answering time to the total (measurement period) can be used as an evaluation value that evaluates the concentration ratio quantitatively. If the total area S is subtracted from the measurement period, the total time (non-concentration time) of the non-concentration state is found.

In order to calculate the evaluation value of the concentration ratio as described above, it is necessary to determine that the parameter of the function f1(t) and the function f2(t) applies to the time occupancy degree histogram. Since the function f1(t) is the probability density function of the log normal distribution, a parameter (average value and distribution) about the function f1(t) is optimizes so that the mountain-shaped region M11 (or mountain-shaped region M21 including the peak P21) including the peak P11 may be suited.

Since the solution space for searching for the parameter optimal about the function f1(t) is vast, the maximum likelihood value of a parameter is calculated using the well-known algorithm like the EM algorithm. The parameter of the function f1(t) is converged in comparatively short time, if the initial value is set appropriately, but the change of the initial value is repeated until the initial value is changed and the parameter completes, in not converging.

The probability density function f1(t) applied to the mountain-shaped region M11 (or M21) of the time occupancy degree histogram approximates the first time occupancy degree histogram. Therefore, if the portion equivalent to the probability density function f1(t) is removed from the time occupancy degree histogram after applying the probability density function f1(t) to the mountain-shaped region M11 (or M21), the histogram equivalent to the second time occupancy degree histogram remains. If the function f2(t) applied to this histogram is calculated, the second time occupancy degree histogram is approximated by the function f2(t).

Figure 6:
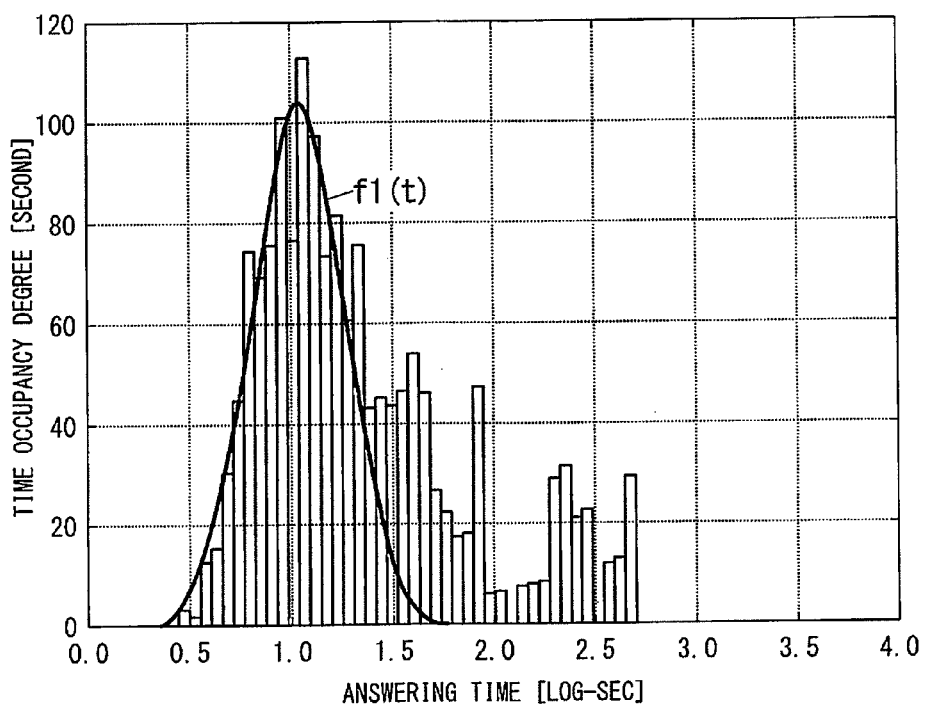
FIG. 6 is a drawing illustrating an example that applied a probability density function in the intellectual-productivity analysis apparatus according to the first embodiment.

The example that applied the probability density function f1(t) approximated to the first time occupancy degree histogram about the time occupancy degree histogram is shown in FIG. 6. That is, in the time occupancy degree histogram, the probability density function f1(t) of the log normal distribution is applied to the candidate of the first time occupancy degree histogram among the mountain-shaped regions with the peak of the time occupancy degree.

In many cases, the candidate of the first time occupancy degree histogram becomes a mountain-shaped region including the peak from that the degree of time occupancy becomes the maximum, but in a test subject with many ratios of the "long-term rest state", the peak from which the degree of time occupancy becomes the maximum may not agree in the first time occupancy degree histogram. Therefore, the applying part 113 (refer to FIG. 1) described below is configured to apply the probability density function f1(t) to the candidate of the first time occupancy degree histogram, for example, by using the following procedures.

It is assumed that the range of the answering time expected here is known. Since there is individual difference in this range, if the rule of thumb of the answering time is measured a priori before measuring the concentration ratio, the range of the answering time can be defined correctly.

The applying part 113 is configured to except, as an abnormal value, extremely short data to the range when the answering time is expected in the time occupancy degree histogram. Then, the applying part 113 is configured to set, to the section of the peak, a section where the time occupancy degree is larger than adjacent sections before and after thereof, and extract the mountain-shaped region including the section of the peak. One or more mountain-shaped regions are extracted.

The applying part 113 is configured to apply the probability density function f1(t) of the log normal distribution for each extracted mountain-shaped region. The applying part 113 is configured to evaluate the degree of conformity using, as conformity degree, the distance (square root of the total of the value of squared difference) between the applied probability density function f1(t) and an actual measurement. When the distance is used for the conformity degree, the probability density function f1(t), in which the distance is the minimum, is adopted.

Since the probability density function f1(t) of the log normal distribution has a mountain shape, it is considered that the probability density function f1(t) suits the mountain-shaped region in the time occupancy degree histogram. That is, in the time occupancy degree histogram, it is expected that the probability density f1(t) suits the region to which the degree of time occupancy becomes small as the distance from a peak enlarges. It is considered that in other words the region that the change in the degree of time occupancy produces frequently has a low degree of conformity with the probability density function f1(t). Therefore, if the evaluation value described above is used, the probability density function f1(t) that suits the first time occupancy degree histogram is defined properly. If the section of the peak excepts beforehand the region exceeding the maximum of the range of the answering time, the time required to the processing of applying the probability density function f1(t) is shortened.

In order to calculate the evaluation value of the concentration ratio as described above, as shown in FIG. 1, the evaluating arithmetic part 110 includes: a histogram generating part 112 configured to generate the time occupancy degree histogram; and an applying part 113 configured to apply the function to the time occupancy degree histogram. The evaluating arithmetic part 110 further includes a calculation part 114 configured to calculate the concentration time or the concentration ratio using one or more parameters of the applied function.

As described above, the applying part 113 is configured to apply the probability density function f1(t) of the log normal distribution to the mountain-shaped regions M11 and M21 that become the candidates of the first time occupancy degree histograms in the time occupancy degree histograms. That is, in an example shown in FIG. 4 (or FIG. 5), the applying part 113 is configured to approximate, with the probability density function f1(t) of the log normal distribution, the mountain-shaped region M11 (or M21) including the peak P11 (or P21) in the time occupancy degree histogram.

The calculation part 114 is configured to extract, as feature amount, an expected value calculated from the probability density function f1(t) of the first log normal distribution. The calculation part 114 is configured to calculate, as a concentration time, the product of this feature amount and the total of the answers. The calculation part 114 is configured to calculate the ratio of the found concentration time to the measurement period as an evaluation value equivalent to the concentration ratio. The calculation part 114 may calculate the value obtained by subtracting the calculated concentration time from the measurement period as the non-concentration time, and may calculate the ratio of the non-concentration time to the measurement period as an evaluation value equivalent to the non-concentration ratio.

The concentration time, the non-concentration time, the evaluation value of the concentration ratio, and the evaluation value of the non-concentration ratio are presented on the presentation device 20 made to serve a double purpose as a display device through the presentation control part 111.

The embodiment described above described while the case is assumed where the presentation device 20 presents the questions by one in order. However, as described above, the answering time can also be measured by using the times between the answers. For example, the time between the time when inputting of the answer of one question (first question) into the input device 30 is finished, and the time when inputting of the answer of the following one question (second question) is finished may be used for the answering time of one question (second question). That is, the time period from the time when the input of the answer of the first question is finished to the time when the input of the answer of the following one question (second question) is finished may be used as the answer time of the second question. When making the answering time into the time during an answer, it is possible to find the answering time, without using the presentation device 20. That is, the answering time is found if the time when a question expressed in paper or the like is presented to a test subject, and makes an answer input into the input device 30 and when an answer finished being input for every question is stored. When the questions described in paper or the like are presented to the test subject, the question does not need to be presented to one sheet by list and may be presented in each one sheet by one question.

Second Embodiment

Although the case where a three-state model is used was described in the first embodiment, an example using simpler two state models will be described in the present embodiment.

Here, a first state where the answering time is in a specified base period is referred to as a "break state". A second state where the answering time exceeds the base period is referred to as a "working state". The working state may be put in another way as the concentration state, and the break state may be put in another way as the non-concentration state. Transition with the working state and the break state is denoted, for example, by a Markov model. It is considered that the break state is further divided into two steps according to the time length of the break state. However, it is assumed the Markov model of two states of the working state and the break state. If such a model is assumed, it is possible to obtain the assumption that the frequency distribution of the answering time reflects two states of the working state and the break state.

Figure 7:
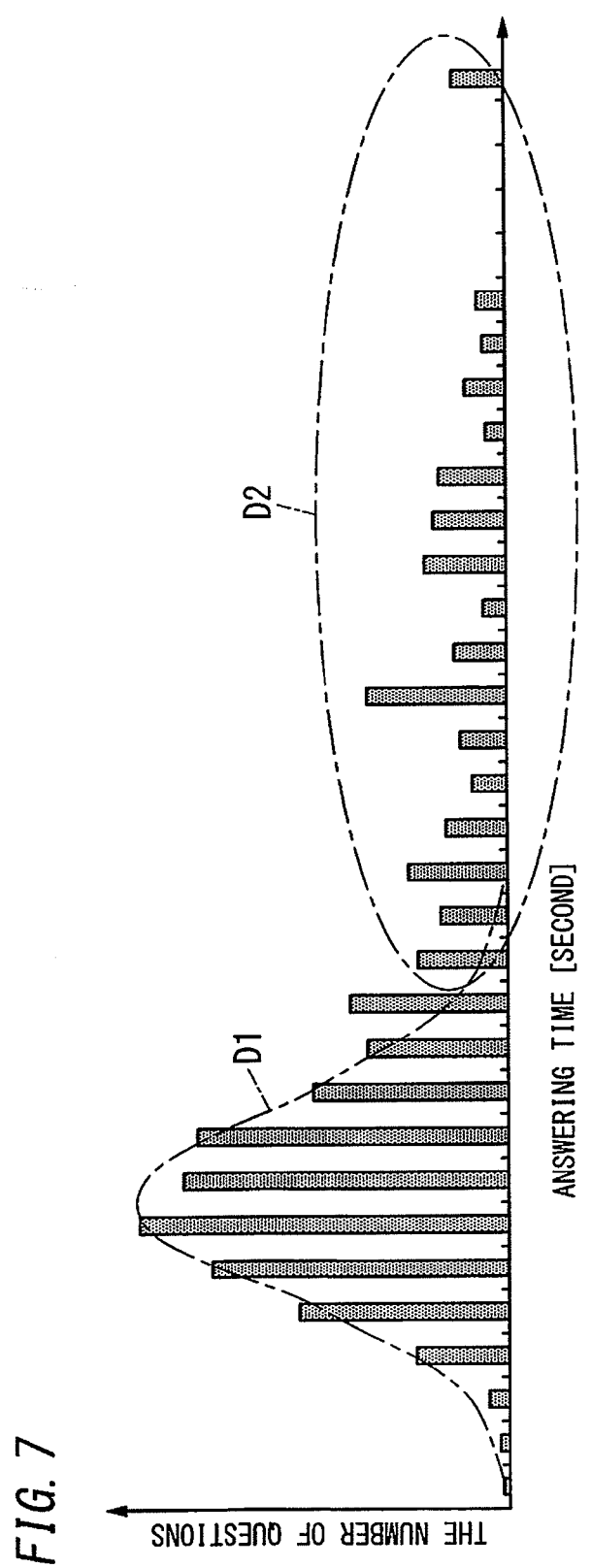
FIG. 7 is a drawing illustrating an example of a histogram used for an intellectual-productivity analysis apparatus according to a second embodiment.

In order to verify this assumption, the frequency distribution is calculated paying attention to the answering time stored in the work memory part 122, and the histogram in which the time-axis is logarithm is produced. Producing of the histogram obtains the result that the region D1 is substantially applied to one log normal distribution as shown in FIG. 7, and the region D2 is not applied to this log normal distribution. That is, the result is obtained, in which, although the region D1 where the answering time is comparatively short is applied to one log normal distribution, the region D2 where the answering time is comparatively long is not applied to this log normal distribution. It is considered that the region D2 that is not applied to the log normal distribution is equivalent to the break state, since having a comparatively long answering time.

Then, the answering time makes among histograms the region D1 which is in the base period the region of the working state, and the answering time makes the region D2 exceeding the base period the region of the break state. The base period is set near the maximum of the region D1 applicable to the log normal distribution. Thus, it is possible by dividing a histogram into the two regions D1 and D2 to extract feature amount from each region D1 and D2.

Figure 8:
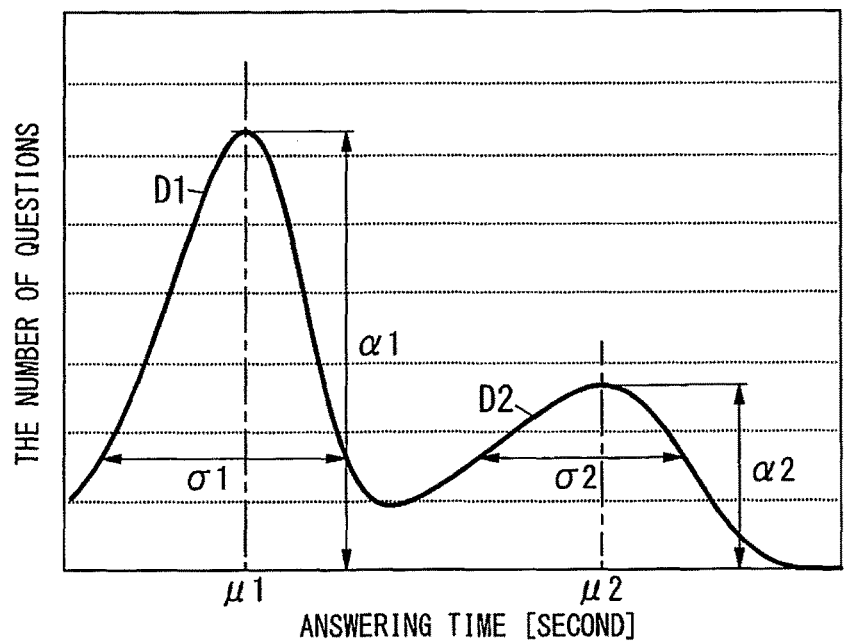
FIG. 8 is a drawing illustrating a model of the histogram in the intellectual-productivity analysis apparatus according to the second embodiment.

Here, as shown in FIG. 8, the model is assumed, which has two peaks of the peak corresponding to the working state and the peak corresponding to the break state as a model of the histogram about the answering time made in a state where the time axis is a time-axis logarithm. This model has two bell type regions like the model of the first embodiment, and it is considered that each of the regions D1 and D2 is applied to the log normal distribution.

However, the present embodiment is different from the first embodiment in that it is considered that the region D2 is the state of the "long-term rest state" in the present embodiment, although it is considered that the region D2 is the state where the "working state", the "short-term rest state", and the "long-term rest state" are mixed in the first embodiment. That is, it is considered that the state of the test subject in the region D1 is the working state (concentration state), and it is considered that the state of the test subject in the region D2 is the break state (non-concentration state).

In this example, the average value µ1 and the standard deviation σ½ are calculated from the region D1 equivalent to the working state, and the average value µ2 and the standard deviation σ2/2 are calculated from the region D2 equivalent to the break state. The peak value α1 of the frequency is calculated for the region D1 equivalent to the working state, and the peak value α2 of the frequency is calculated for the region D2 equivalent to the break state. By using these parameters (µ1, µ2, σ1, σ2, α1, α2), the feature amount that makes dividable the region D1 of the working state and the region D2 of the break state is obtained as follows.

That is, when the model shown in FIG. 8 is assumed, the ratio that the area of the region equivalent to the working state occupies to the whole surface product of the histogram, and the ratio which in other words the frequency when the answering time is equal to or less than a predetermined threshold occupies to the total in question can be said to be being the ratio of a period which was in the concentration state during measurement. If this ratio is calculated as the feature amount, the rule of thumb of the concentration time at the time of the test subject working is obtained. As the rule of thumb of the concentration time, the ratio (=α1/α2) of the peak value α1 of the working state to the peak value α2 of the break state may be used as the feature amount. That is, the evaluation value of the length of the concentration time is calculated using the frequency of the answering time of the region equivalent to the working state.

The ratio (=2α1/σ1) of the peak value α1 to the standard deviation σ½ of the region equivalent to the working state, or the standard deviation σ½ expresses the kurtosis of the region equivalent to the working state, and is considered that the kurtosis of the form of this region reflects the concentration ratio. Therefore, the standard deviation σ½ or the ratio 2α1/σ1 is calculated as concentration strength of the concentration time.

Incidentally, the method of calculating the parameter (µ1, µ2, σ1, σ2, α1, α2) of the model shown in FIG. 8 from the histogram of the answering time as shown in FIG. 7 cannot be formulated. Therefore, various combination of a parameter is generated and the parameter which is best applied to a histogram is chosen. Since the huge time is required when extracting a parameter if a round robin algorithm is used in order to generate various combinations of parameters, it is desirable to use for selection of parameters an EM algorithm described above or a genetic algorithm.

As described above, the evaluating arithmetic part 110 is configured to calculate the frequency distribution of the answering time using the answering time stored in the work memory part 122, and extract the region equivalent to the working state and the region equivalent to the break state about the histogram made into the logarithm axis the time-axis of this frequency distribution. The evaluating arithmetic part 110 is configured to calculate the evaluation value of the concentration time and the evaluation value of the concentration strength by using the parameter of the region equivalent to the working state and the region equivalent to the break state. It means that the evaluating arithmetic part 110 is configured to calculate the evaluation value about the intellectual productivity since these evaluation values are concerned with the intellectual productivity. The histogram that generated by the evaluating arithmetic part 110, the parameters (µ1, µ2, σ1, σ2, α1, α2) obtained from the histogram, and the evaluation value calculated from the histogram are displayed on the display device that serves as the presentation device 20 if needed. Other configurations and operations are the same as those of the first embodiment.

When the evaluation device 10 communicates with another device 40, such as a server, via the third I/F part 133, it is possible by transmitting a question to the question storage part 121 from the device 40 to update a question as required. The function of the evaluation device 10 may be provided to the device 40, such as a server, and an intellectual-productivity analysis apparatus may be constituted of the device 40 and a device provided with the presentation device 20, the input device 30, and the I/F part 13.

Each embodiment described above is an example of the present invention. For this reason, if the present invention is not limited to each embodiment described above, and a range that does not deviate from the technical idea concerning the present invention even if an embodiment is other than these embodiments, various change is possible according to a design, for example.

(Verification)

If the intellectual-productivity analysis apparatus described above is used, it is possible to measure the evaluation value about the concentration ratio at the time of performing a mental task. Therefore, it is considered that it is useful in order to define conditions suitable for the mental task if various conditions such as the environmental element of working space or a rest time are changed and the concentration ratio is measured quantitatively.

Figure 9:
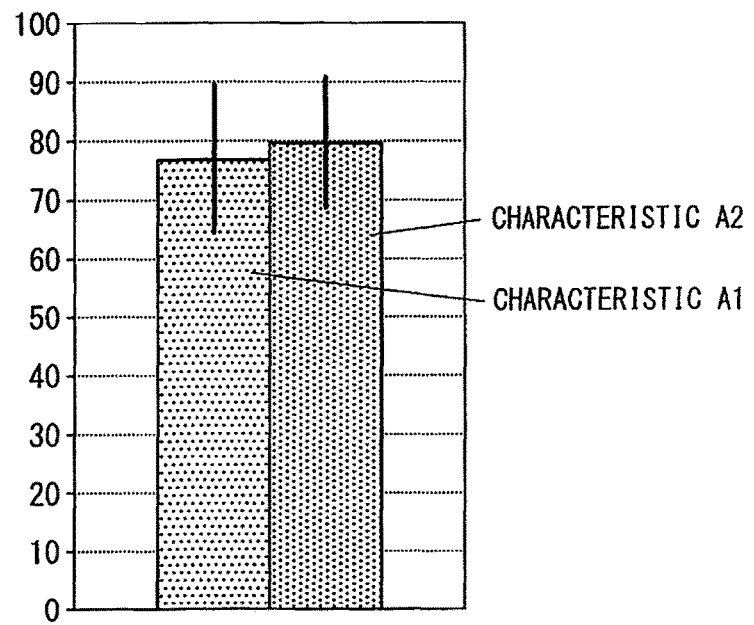
FIG. 9 is a drawing illustrating an example that measured the relation between lighting environment and a concentration ratio using the intellectual-productivity analysis apparatus according to the second embodiment.

In order to verify this, the concentration ratio of the test subject in two kinds of different lighting environment was measured. One lighting environment adopted the base lighting used in many offices, and the lighting environment of another side used the ambient lighting and task illuminations together. The concentration ratio was measured using the intellectual-productivity analysis apparatus described in the second embodiment while a test subject was made to perform a word classification task in each lighting environment. FIG. 9 shows the result of the measurement.

According to FIG. 9, although the difference of the concentration ratio (=concentration time/measurement period) was minute, the result that the concentration ratio increased as compared with the case (characteristic A1 of FIG. 9) where only base lighting is used in the way at the time of using the Ambient lighting and task illuminations together (characteristic A2 of FIG. 9) was obtained.

The result that the way at the time of instructing the former had the high concentration ratio was obtained the test subject by the case where the instruction "tackle intensively" is performed, and the case where the instruction "tackle at the usual pace" is performed. Indoor environment was made into the same condition on the occasion of the measurement of the concentration ratio to an instruction different here.

Since the two results described above are not contrary to the knowledge generally recognized, it is shown that the measurement of the concentration ratio is possible by the intellectual-productivity analysis apparatus described above.

(Example of Use)

When performing a prolonged intellectual work, the intellectual-productivity analysis apparatus described above can be used in order to measure transition of the concentration ratio accompanying temporal passage. That is, it is possible to calculate the change of the concentration ratio of the test subject by calculating the evaluation value of the concentration ratio during the several different measurements about the test subject. The factor that changes the concentration ratio includes a lapse of time at which the intellectual work is performed, and an indoor environment in which the intellectual work is performed, for example. The evaluation value of the concentration ratio is calculated as a ratio of the concentration time to a measurement period (total time), as described above.

Figure 10:
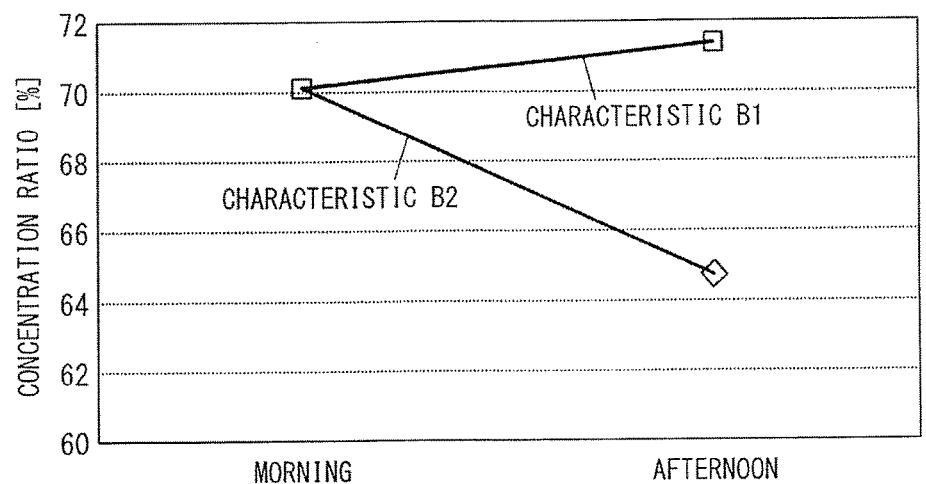
FIG. 10 is a drawing illustrating an example in which a change of a concentration ratio is calculated in the intellectual-productivity analysis apparatus according to the second embodiment.

For example, if the concentration ratio for first thirty minutes and the concentration ratio for the last thirty minutes are measured when the test subject is performing the intellectual work through one day, it is possible to measure quantitatively deterioration of the concentration ratio of the test subject or the degree of improvement. FIG. 10 is an example at the time of measuring the concentration ratio in the morning and the afternoon, respectively, changes indoor environment and is making the test subject work in the characteristic B1 and the characteristic B2. The characteristic B1 shows the example in which the concentration ratio improves, and the characteristic B2 shows the example for which the concentration ratio is deteriorated. On the other hand in this example, when indoor environment differs to the concentration ratio having been about 70% during the morning shows that the concentration ratio improves to about 71.5%, and the concentration ratio is deteriorated to about 65% on the other hand.

If the concentration ratio is measured by processing described above, transition of the concentration ratio in the measurement period when the test subject is performing question is immeasurable. Then, in order to determine the rule of thumb of the concentration ratio simply, the intellectual-productivity analysis apparatus may determine the first state (concentration state) and the second state (non-concentration state) by setting the base period to the answering time and comparing the answering time with the base period in connection with the temporal passage of the measurement period.

That is, in the first embodiment and the second embodiment, since using the histogram, the intellectual-productivity analysis apparatus cannot extract the information about the change of the concentration ratio accompanying the temporal passage of the measurement period. On the other hand, since comparing the answering time with the base period in connection with the temporal passage of the measurement period, the intellectual-productivity analysis apparatus can measure simply the change of the concentration ratio accompanying the temporal passage during the measurement period.

Since being not the result of the statistical work to the set of the answering time unlike the first embodiment and the second embodiment, the result of having compared the answering time with the base period in connection with the temporal passage of the measurement period cannot be used in order to measure the concentration ratio quantitatively. However, it is possible to use for the purpose of obtaining the rule of thumb of transition of state of a between the concentration state when the test subject answers on a question the non-concentration state.

The calculation part 114 is configured to determine the concentration state and the non-concentration state. That is, the calculation part 114 is configured to perform processing of comparing the answering time read from the work memory part 122 with the base period. The evaluating arithmetic part 110 is configured to generate the data for presenting the result calculated by the calculation part 114 on the presentation device 20 as a graph shown in FIG. 11. That is, the result calculated by the calculation part 114 is outputted to the presentation device 20 through the first I/F part 131.

Figure 11:
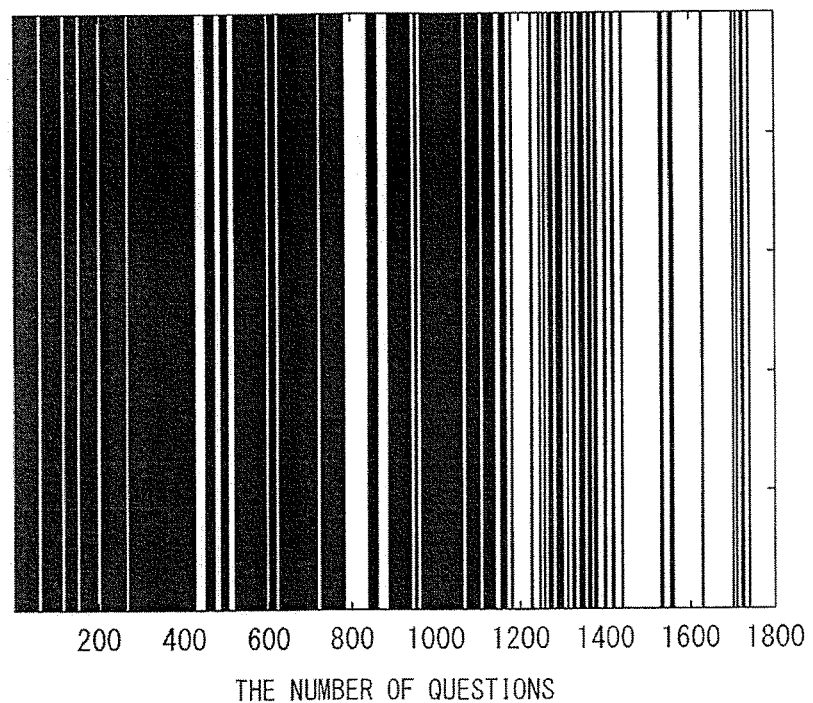
FIG. 11 is a drawing illustrating an example in which the change of state of the measurement period is calculated in the intellectual-productivity analysis apparatus according to the second embodiment.

FIG. 11 shows an illustrated example that expressed black areas in the case where the answering time is equal to or less than the base period and white regions in the case where the answering time exceeded the base period when makes a horizontal axis is made to be the accumulated (elapsed time may be sufficient) of the number of questions. In this display example, a black area shows the rule of thumb of the concentration state, and the white region shows the rule of thumb in the non-concentration state. Although the result per question may be made to reflect, about the majority of two or more questions, a black area and a white region is made into a black area, for example, if the answering time is equal to or less than the base period, and if the question, of which the answering time is equal to or less than the base period, is equal to or less than the moiety, a white region may be used.

If such a display is enabled, it is possible to obtain the rule of thumb of transition of the concentration condition of the test subject with the elapsed time. Therefore, for example, it is possible to use for a measurement of a time during which the concentration state continues.

The invention claimed is:

1. An intellectual-productivity analysis apparatus comprising:
a presentation device configured to present a plurality of questions to a test subject;
an input device configured to allow the test subject input an answer to each of the plurality of questions; and
an evaluation device configured to measure an answering time from a time when a question is presented on the presentation device for each of the plurality of questions to a time when the answer is inputted into the input device, the evaluation device being configured to calculate an evaluation value on an intellectual productivity of the test subject using a set of the answering time,
wherein the evaluation device comprises:
a work memory part configured to store the answering time for each of the plurality of questions; and
an evaluating arithmetic part configured to calculate an evaluation value on the intellectual productivity of the test subject during a measurement period of measuring the answering time of each of the plurality of questions by extracting a feature amount from the set of the answering time stored in the work memory part,
wherein the evaluating arithmetic part comprises:
a histogram generating part configured to classify the answering time into a plurality of sections, the histogram generating part being configured to regard, as a time occupancy degree, a ratio of a total of the answering time in a section to a total of the answering time for each of the plurality of sections, the histogram generating part being configured to generate a time occupancy degree histogram expressing distribution of the time occupancy degree;
an applying part configured to regard the time occupancy degree histogram as a superimposition of a first time occupancy degree histogram in a state where a working state and a short-term rest state are mixed, and a second time occupancy degree histogram in a state where the working state, the short-term rest state, and a long-term rest state are mixed, the applying part being configured to apply a probability density function of a log normal distribution to a candidate of the first time occupancy degree histogram among mountain-shaped regions with a peak of the time occupancy degree; and
a calculation part configured to extract an expected value calculated from the probability density function as the feature amount, and calculate, as a concentration time, a product of the feature amount and a total number of the answers, the calculation part being configured to calculate the concentration time to the measurement period as the evaluation value.

2. The intellectual-productivity analysis apparatus according to claim 1, wherein the applying part is configured to apply, to the probability density function, a region where the time occupancy degree is not only smaller than the peak but also shorter than the answering time corresponding to the peak among the mountain-shaped regions.

3. The intellectual-productivity analysis apparatus according to claim 2, wherein the calculation part is configured to calculate a value obtained by subtracting the concentration time from the measurement period as a non-concentration time in the measurement period.

4. The intellectual-productivity analysis apparatus according to claim 2,
wherein the evaluating arithmetic part is configured to calculate a ratio of the concentration time to the measurement period as an evaluation value of a concentration ratio,
the evaluating arithmetic part being configured to calculate a change of the concentration ratio of the test subject in two or more measurement periods.

5. The intellectual-productivity analysis apparatus according to claim 1, wherein the applying part is configured to, after applying the probability density function to the mountain-shaped regions, calculate a histogram except a portion equivalent to the probability density function from the time occupancy degree histogram, the applying part being configured to calculate a function applied to the histogram.

6. The intellectual-productivity analysis apparatus according to claim 5,
wherein the evaluating arithmetic part is configured to calculate a ratio of the concentration time to the measurement period as an evaluation value of a concentration ratio,
the evaluating arithmetic part being configured to calculate a change of the concentration ratio of the test subject in two or more measurement periods.

7. The intellectual-productivity analysis apparatus according to claim 1, wherein the calculation part is configured to calculate a value obtained by subtracting the concentration time from the measurement period as a non-concentration time in the measurement period.

8. The intellectual-productivity analysis apparatus according to claim 1,
wherein the evaluating arithmetic part is configured to calculate a ratio of the concentration time to the measurement period as an evaluation value of a concentration ratio,
the evaluating arithmetic part being configured to calculate a change of the concentration ratio of the test subject in two or more measurement periods.

9. The intellectual-productivity analysis apparatus according to claim 1, further comprising a display device configured to display, on a screen, a graph showing the answering time and the evaluation value calculated by the evaluating arithmetic part.

10. The intellectual-productivity analysis apparatus according to claim 1, wherein the presentation device and the input device are integrally provided with the evaluation device.

11. The intellectual-productivity analysis apparatus according to claim 10,
wherein the feature amount is:
a ratio of a total of frequency when the answering time is in the base period to a total of the plurality of questions; and
a standard deviation calculated by applying to a log normal distribution, frequency distribution when the answering time is in the base period, and
wherein the evaluating arithmetic part is configured to calculate the ratio as an evaluation value expressing a length of a time period of the first state,
the evaluating arithmetic part being configured to calculate the standard deviation as an evaluation value expressing a concentration ratio of the time period of the first state.

12. The intellectual-productivity analysis apparatus according to claim 1, wherein the feature amount is an amount so that a first state where the answering time is in a base period is dividable from a second state where the answering time exceeds the base period.

13. The intellectual-productivity analysis apparatus according to claim 1, wherein the evaluating arithmetic part is configured to calculate a first state where the answering time is in a base period and a second state where the answering time exceeds the base period according to a time course of the measurement period.

14. The intellectual-productivity analysis apparatus according to claim 1, wherein the applying part is configured to, after applying the probability density function to the mountain-shaped regions, calculate a histogram except a portion equivalent to the probability density function from the time occupancy degree histogram, the applying part being configured to calculate a function applied to the histogram.

15. The intellectual-productivity analysis apparatus according to claim 1, wherein the calculation part is configured to calculate a value obtained by subtracting the concentration time from the measurement period as a non-concentration time in the measurement period.

16. The intellectual-productivity analysis apparatus according to claim 1,
wherein the evaluating arithmetic part is configured to calculate a ratio of the concentration time to the measurement period as an evaluation value of a concentration ratio,
the evaluating arithmetic part being configured to calculate a change of the concentration ratio of the test subject in two or more measurement periods.

17. A non-transitory computer-readable recording medium having stored therein a program to function a computer as an evaluation device configured to make a presentation device present a plurality of questions and allow a test subject input an answer to each of the plurality of questions into an input device, the evaluation device being configured to measure an answering time from a time when a question is presented on the presentation device for each of the plurality of questions to a time when the answer is inputted into the input device, the evaluation device being configured to calculate an evaluation value on an intellectual productivity of the test subject using a set of the answering time,
wherein the program functions the computer as the evaluation device comprises:
a work memory part configured to store the answering time; and
an evaluating arithmetic part configured to calculate an evaluation value on the intellectual productivity of the test subject during a measurement period of measuring the answering time of each of the plurality of questions by extracting a feature amount from the set of the answering time stored in the work memory part, wherein the evaluating arithmetic part comprises:

a histogram generating part configured to classify the answering time into a plurality of sections, the histogram generating part being configured to regard, as a time occupancy degree, a ratio of a total of the answering time in a section to a total of the answering time for each of the plurality of sections, the histogram generating part being configured to generate a time occupancy degree histogram expressing distribution of the time occupancy degree;

an applying part configured to regard the time occupancy degree histogram as a superimposition of a first time occupancy degree histogram in a state where a working state and a short-term rest state are mixed, and a second time occupancy degree histogram in a state where the working state, the short-term rest state, and a long-term rest state are mixed, the applying part being configured to apply a probability density function of a log normal distribution to a candidate of the first time occupancy degree histogram among mountain-shaped regions with a peak of the time occupancy degree; and a calculation part configured to extract an expected value calculated from the probability density function as the feature amount, and calculate, as a concentration time, a product of the feature amount and a total number of the answers, the calculation part being configured to calculate the concentration time to the measurement period as the evaluation value.

* * * * *